Figure 1:
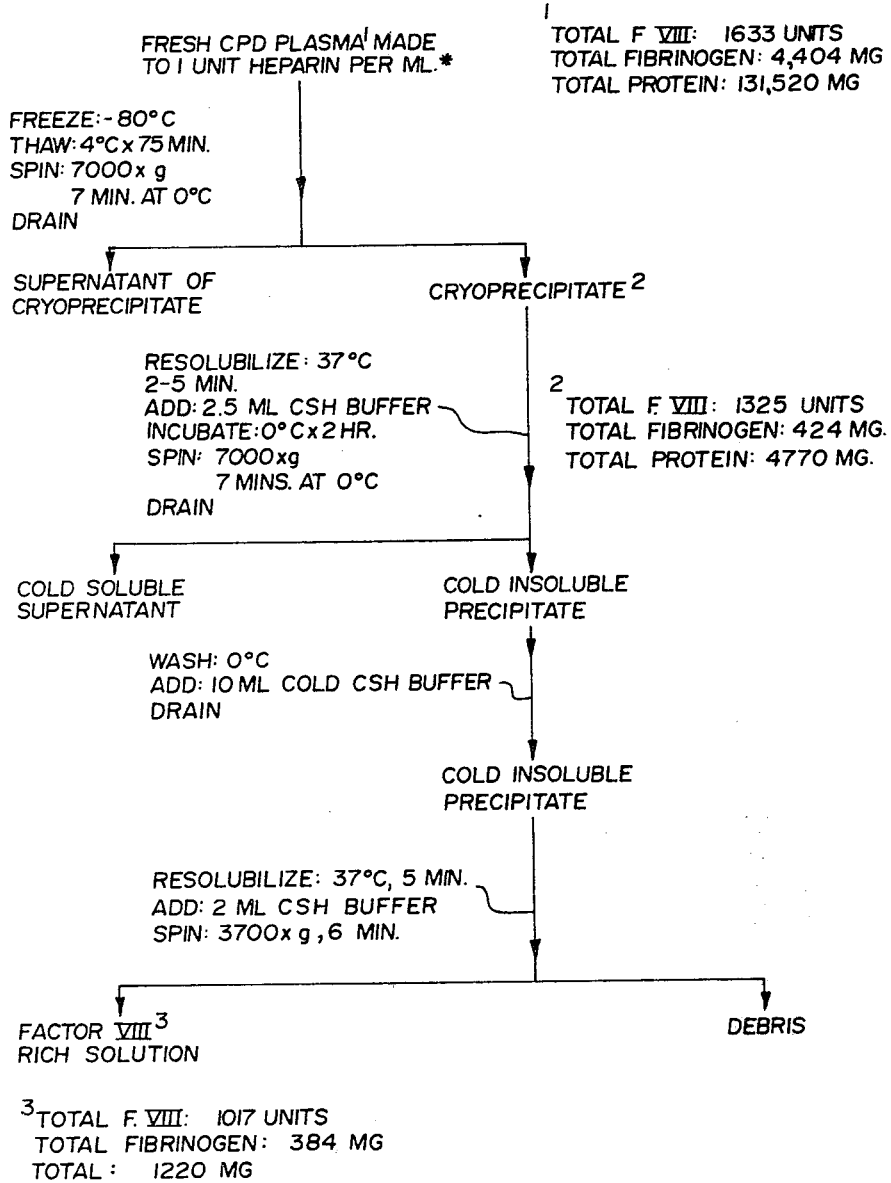

United States Patent [19]

Rock et al.

[11] 4,289,691

[45] Sep. 15, 1981

[54] METHOD OF OBTAINING INTERMEDIATE PURITY FACTOR VIII

[75] Inventors: Gail A. Rock, 270 Sandridge Rd., Rockcliffe Park, Canada, K1L 5A2; Douglas S. Palmer, 17 Front St., Hull, Canada, J8Y 3M4

[73] Assignees: The Canadian Red Cross Society, Toronto; Gail Ann Rock, Rockcliffe Park; Douglas Stephen Palmer, Hull, all of Canada

[21] Appl. No.: 210,385

[22] Filed: Nov. 26, 1980

Related U.S. Application Data

[63] Continuation-in-part of Ser. No. 123,472, Feb. 21, 1980, abandoned.

[30] Foreign Application Priority Data

Jan. 18, 1980 [CA] Canada ................................. 344000

[51] Int. Cl.$^3$ .............................................. C07G 7/00
[52] U.S. Cl. ............................. 260/112 B; 424/101; 424/177; 424/183
[58] Field of Search .................... 260/112 B; 424/101, 424/177, 183

[56] References Cited

U.S. PATENT DOCUMENTS

| Re. 29,698 | 7/1978 | Fekete et al. | 260/112 B |
|---|---|---|---|
| 3,803,115 | 4/1974 | Fekete et al. | 260/112 B |
| 4,022,758 | 5/1977 | Andersson et al. | 260/112 B |
| 4,104,266 | 8/1978 | Wickerhauser | 260/112 B |
| 4,203,891 | 5/1980 | Rock | 260/112 B |

OTHER PUBLICATIONS

J. Clin. Invest., 36:596–604 (1957), Smith et al.
J. Clin. Invest., 36:605–616 (1957), Smith.
J. of Biol. Chem. 250:6614–6621 (1975), Mosher.
Proc. Soc. Exp. Biol. Med. 86:813–819 (1954), Thomas et al.
Transfusion 19:14 299–306 (1979), Smith et al.
J. Clin. Invest. 60:855–865 (1977), Stathakis et al.
Blood 6:14 1211–1222 (1978), Stathakis et al.
J. of Biol. Chem. 245:5728–5736 (1970), Mosesson et al.

*Primary Examiner*—Howard E. Schain
*Attorney, Agent, or Firm*—Holman & Stern

[57] ABSTRACT

A method of obtaining Factor VIII which comprises
(a) adding heparin to freshly obtained blood plasma collected into a calcium chelating anticoagulant or collecting blood plasma by plasma pheresis using heparin and a calcium chelating anticoagulant;
(b) freezing the plasma;
(c) resolubilizing the plasma;
(d) isolating a cryoprecipitate from the plasma;
(e) resolubilizing the cryoprecipitate;
(f) adding a citrate saline heparin buffer to the resolubilized cryoprecipitate;
(g) incubating the buffered, resolubilized cryoprecipitate at a temperature of from about 0° to about 10° C. for a time in excess of about one hour, whereby Factor VIII present in the cryoprecipitate is insolubilized using heparin precipitable cold insoluble globulin and the resulting Factor VIII rich precipitate also includes cold insoluble globulin;
(h) separating the Factor VIII rich precipitate; and
(i) isolating Factor VIII therefrom.

The introduction of the cold insoluble globulin (CIg) step to Factor VIII production results in markedly increased yields of Factor VIII in the cryoprecipitate and, as well, in the cold-insoluble globulin obtained from the cryoprecipitate. Using this procedure, 81% of the Factor VIII is recovered in the cryoprecipitate. The cold-insoluble globulin contains 62% of the starting Factor VIII activity. A final recovery of 666 units per liter of starting plasma is therefore obtained and the amount of protein is reduced to less than 1%. In addition, the procedure can be carried out in blood donor centers, although it is also envisaged to be useful in larger scale recovery of Factor VIII procedures.

16 Claims, 1 Drawing Figure

METHOD OF OBTAINING INTERMEDIATE PURITY FACTOR VIII

This application is a continuation-in-part application of U.S. application Ser. No. 123,472, filed Feb. 21, 1980, now abandoned.

This invention is concerned with a method of obtaining Factor VIII without the use of chemical precipitating agents. The technique relies on the heparin-induced coprecipitation of Factor VIII with a plasma protein called cold-insoluble globulin (CIg).

In 1954, Thomas et al in a paper entitled "Cold precipitation by heparin of a protein in rabbit and human plasma" Proc. Soc. Exp. Biol. Med. 86: 813–819 reported the occurrence of heparin-induced cold or cryoprecipitate plasma from endotoxin-treated rabbits. This fraction has since come to be known as the heparin precipitable fraction of plasma. Subsequent studies reported in 1957 by Smith and Von Korff in a paper entitled "A heparin-precipitable fraction of human plasma. I. Isolation and characterization of the fraction." J. Clin. Invest. 36: 596–604 and Smith in a paper entitled "A heparin-precipitable fraction of human plasma II. Occurrence and significance of the fraction in normal individuals and in various disease states." J. Clin. Invest., 36: 605–616, showed that large amounts of this cold precipitable fraction were formed from plasmas of patients with certain inflamatory infectious and neo-plastic diseases when heparin was added to the plasma. In normal donors the amount produced was usually less. At this time it was established that fibrinogen was a major component of this fraction. A second minor component of the fraction was also observed which was termed "cold-insoluble globulin". This cold-insoluble globulin (CIg) is known to be a normal plasma glycoprotein that is structurally and immunochemically distinct from fibrinogen and all other plasma proteins. CIg normally circulates at plasma levels of 0.33±0.1 g/liter. Cold-insoluble globulin in its various forms has been designated by a variety of terms, of which "fibronectin" has recently become most accepted (The Structure and Biologic Activities of Plasma Fibronectin, Mosesson, et al, Blood, Volume 56, No. 2, pages 145-158).

In 1974, U.S. Pat. No. 3,803,115 was issued to Fekete et al for a method of improving the yield of Factor VIII or A.H.F. obtained from blood plasma or plasma fractions which involved the addition of heparin to a concentrate of A.H.F. obtained from the plasma or plasma fraction by cryoprecipitation. This patent was reissued July 11, 1978 under U.S. Pat. No. Re 29698. In the reissue patent, Fekete et al indicate that the addition of heparin is made to an A.H.F. concentrate obtained from blood plasma or a plasma fraction by cryoprecipitation which may then be further fractionated to obtain an even more concentrated form of A.H.F. In the reissue patent, column 2, lines 36 et al, it is indicated that the heparin is preferably added to the A.H.F. rich concentrate in addition to citrate. A preferred method of conducting the double anticoagulant addition is to add the heparin to the cryoprecipitate in the form of a heparinized, citrated-saline solution. When the A.H.F. rich cryoprecipitate is further fractionated to obtain a high purity, more concentrated form of A.H.F., heparin is preferably added twice, once to the initial cryoprecipitate and subsequently to the further fractionated A.H.F. concentrate. In each case, heparin is preferably added along with citrate as a second anticoagulant.

It is especially important to note that in the original Fekete patent and the reissue patent, the plasma is received frozen from a donor centre and then a cryoprecipitate step is performed before the heparin is added. Heparin is added only to the cryoprecipitate or to the concentrate of A.H.F. after cryoprecipitation occurs. Reference should also be made to Col. 4 of the Fekete reissue patent, lines 46–49 wherein it is clear from the temperatures at which the cryoprecipitate is resolubilized, the CIg or fibronectin is lost and therefore unavailable to aid in the recovery of Factor VIII. According to Fekete, the yield of Factor VIII is improved from 13.6 or 12.5% in the non-heparinized procedure to 17% in the heparinized procedure. Fekete indicates that this increase of approximately 4% represents a 25% increase over the non-heparinized procedure. However, as the Table found in column 5 of the patent, Example 1, would indicate, the total yield from the cryoprecipitate is low at 35%, representing only 350 units per liter of starting plasma. Therefore, the 17% recovery in the final product represents only 170 units per liter of starting plasma. These calculations are based on the international reference standard of one unit per ml of plasma.

It will be clear from the above discussion that the cold precipitation of fibronectin and fibrinogen had been an established procedure for many years prior to the filing date of the original Fekete patent in 1972. It was generally known that addition of heparin or some other polysaccharide compound was necessary in order to effect precipitation of fibronectin in the cold. However, at no point has the literature suggested or contained directions for the application of a cold-insoluble globulin or fibronectin step toward the production of Factor VIII. In fact, a 1975 paper by Mosher, entitled "Cross Linking of Cold-Insoluble Globulin by Fibrin-Stabilizing Factor", published in J.B.C. 250: 6614, 1975, indicated that cold-insoluble globulin was distinguished from antihemophilic factor (Factor VIII) by amino acid analysis and by the position of elution from 4% agarose gels and by the electrophoretic migration in polyacrylamide gels.

Thus the present invention deals with the application of a procedure for production of fibronectin or cold-insoluble globulin (CIg) to the production of Factor VIII. The introduction of the cold-insoluble globulin cryoprecipitation step to Factor VIII production results in markedly increased yields of Factor VIII in the cryoprecipitate and, as well, in the cold-insoluble globulin obtained from the cryoprecipitate. Using this procedure, 81% of the Factor VIII is recovered in the cryoprecipitate. The cold-insoluble globulin contains 62% of the starting Factor VIII activity. A final recovery of 666 units per liter of starting plasma is therefore obtained and the amount of protein is reduced to less than 1%. In addition the procedure can be carried out in blood donor centers, although it is also envisaged to be useful in larger scale recovery of Factor VIII procedures.

Thus, the present invention provides a method of obtaining Factor VIII which comprises (a) adding heparin to freshly obtained blood plasma collected into a calcium chelating anticoagulant or collecting blood plasma by plasmapheresis using heparin and a calcium chelating anticoagulant;

(b) freezing the plasma;

(c) resolubilizing the plasma;

(d) isolating a cryoprecipitate from the plasma;

(e) resolubilizing the cryoprecipitate;

(f) adding a citrate saline heparin buffer to the resolubilized cryoprecipitate;

(g) incubating the buffered, resolubilized cryoprecipitate at a temperature from about 0° to about 10° C. for a time in excess of about one hour, whereby Factor VIII present in the cryoprecipitate is insolubilized using heparin precipitable cold insoluble globulin and the resulting Factor VIII rich precipitate also includes cold insoluble globulin;

(h) separating the Factor VIII rich precipitate; and (i) isolating Factor VIII therefrom The calcium chelating anticoagulant can be selected from any of the well known anticoagulants which function by lowering the physiological level of calcium in the blood or blood plasma. Preferred types of such anticoagulants are the citrate anticoagulants, ethylenediaminetetraacetic acid (EDTA), and oxalates. Of these, the citrate anticoagulants are preferred. The preferred citrate anticoagulants include acid-citrate-dextrose (ACD) and citrate-phosphate-dextrose (CPD).

The essential steps of the method of this invention are the addition of the citrate saline heparin (CSH) buffer to the resolubilized cryoprecipitate and the incubation of the cryoprecipitate.

The buffer is preferably added in amounts ranging from about 2 to about 10 ml per cryoprecipitate bag. More preferably, it is added in amounts from about 2 to about 4 ml per cryoprecipitate bag and most preferably, an addition of 2.5 ml per cryoprecipitate bag is made. The buffer preferably has a composition of 0.2 M sodium citrate, 0.9% by weight of sodium chloride and 1 unit per ml of buffer of sodium heparin. The pH of the buffer is maintained at 7.2.

The incubation, as stated before, is carried out at about 0° to about 10° C. for a time in excess of about one hour. Preferably, it is conducted at 0° C. for about two hours.

Cold insoluble globulin (CIg) is not insolubilized after treatment of CPD plasma with heparin. The precipitate of the CIg is not formed until a specific set of conditions are met. Thus, while these conditions include introduction of heparin to fresh CPD plasma, this is not sufficient in itself to produce CIg. Indeed, visual observation indicates that this step alone does not produce the CIg since, when present, this material is seen as a white deposit at the bottom of a blood bag. These steps are the addition of the CSH buffer to the cryoprecipitate and the cold incubation step which permits formation of the precipitating globulin. If these combined steps are not employed, cold insoluble globulin is not formed even in the presence of heparin.

More specifically, the invention may be characterized as a method of obtaining Factor VIII which comprises (a) adding heparin to freshly obtained blood plasma collected into a citrate-phosphate-dextrose anticoagulant or collecting blood plasma by plasmapheresis using heparin and sodium citrate anticoagulant;

(b) freezing the plasma to about −80° C.;

(c) resolubilizing the plasma at a temperature from about 0° to about 10° C. for from about 30 to about 120 minutes, preferably at about 4° C. for about 75 minutes;

(d) centrifuging the resolubilized plasma to isolate a cryoprecipitate;

(e) resolubilizing the cryoprecipitate at a temperature of about 37° C. for about 2–5 minutes;

(f) adding from about 2 to about 10 ml citrate saline heparin buffer to each resolubilized cryoprecipitate bag;

(g) incubating the buffered, resolubilized cryoprecipitate at about 0° C. for about two hours, whereby Factor VIII present in the cryoprecipitate is insolubilized using heparin precipitable cold insoluble globulin, the resulting Factor VIII rich precipitate also including cold insoluble globulin;

(h) separating the Factor VIII rich precipitate; and (i) isolating the Factor VIII therefrom.

Factor VIII may be isolated from the Factor VIII rich precipitate by washing the insoluble precipitate in the cold at a temperature of from about 0° C. to about 10° C., preferably at about 0° C. with citrate saline heparin buffer. The precipitate is then drained and resolubilized with further citrate saline heparin buffer, preferably at about 37° C. for 2 to 5 min. The Factor VIII rich solution can then be separated from the remaining debris, most easily by centrifugation. The Factor VIII rich solution obtained will be of intermediate purity when the starting plasma is obtained from whole blood from which the red blood cells have been separated. In the case where the starting plasma is pheresis plasma, the Factor VIII will have an activity which qualifies it as high purity.

Alternatively or when required, the Factor VIII rich precipitate can be subjected to conventional processes for obtaining high purity Factor VIII, examples of which are fractionation by precipitation, by glycine, ethanol, ethanol-glycine, polyethylene glycol, or glycine-polyethylene glycol precipitation and/or other known purification agents.

The heparin is preferably added at a concentration of 1 unit heparin per ml of plasma. Although a range of from about 1 to about 10 units heparin per ml of plasma is effective. Sodium heparin has proved effective in this method.

The method in precise terms involves freezing the fresh CPD plasma with the heparin added thereto at −80° C. and then resolubilizing at 4° C. for 75 minutes, after which it is centrifuged (spin 7000×g, 7 min. at 0° C.). The resulting cryoprecipitate is allowed to resolubilize at 37° C. for 2–5 minutes, after which 2.5 ml of CSH (citrate saline heparin) buffer is added per cryoprecipitate bag. The resolubilized, pooled cryoprecipitate is then incubated at 0° C. for two hours in a refrigerated water bath. The Factor VIII present in the cryoprecipitate pool now insolubilizes along with the cold-insoluble globulin, and the total insoluble precipitate is then separated from the Factor VIII poor supernatant by centrifugation (spin 7000×g, 7 min. at 0° C.). After draining off the supernatant, the cold-insoluble precipitate is washed at 0° C. with 10 ml of cold CSH buffer, drained and allowed to resolubilize at 37° C. for five minutes with from 2–10 ml, preferably two ml of CSH buffer per original cryoprecipitate bag. A further centrifugation (spin 3700×g, 6 min.) is conducted and the Factor VIII rich solution is separated from the debris.

In the enclosed drawing which is used to illustrate the present invention FIG. 1 is a schematic drawing of the specific steps of the method of the invention, the particular steps being illustrated for a pool of six units of plasma. The previous specifically described method is illustrated by this drawing.

In the following Table 1, there is provided an analysis of the method of the invention. It will be seen that one unit of sodium heparin per ml of freshly obtained human blood plasma was added. Six bags or units of plasma were used to illustrate the method. The table sets out the total units of Factor VIII present in each of the fractions: starting plasma, cryoprecipitate pool and cold-insoluble precipitate as well as the total weight of protein, the specific activity of the Factor VIII units per milligram of protein, the purity of the Factor VIII and the volumes of each of the fractions.

TABLE 1

CPD Plasma + 1 U Heparin/ml² (6 Bags)

| Fraction[1] | Total F. VIII (Units, U) | Total Protein (mg) | Specific Activity (U/mg) | Purity Over Plasma | Volume (ml) |
|---|---|---|---|---|---|
| 1. Starting Plasma | 1633 Units (100%)[3] | 131,520 (100%) | .0124 | 1 x | 1527 ml (100%) |
| 2. Cryoprecipitate Pool | 1325 (81%) | 4770 (3.6%) | .278 | 22.4 x | 53 ml (3.5%) |
| 3. Cold Insoluble Precipitate | 1017 (62%) | 1220 (0.9%) | .834 | 67.25 x | 11.3 ml (0.7%) |

[1]Fraction 2 was obtained from Fraction 1, and Fraction 3 was obtained from Fraction 2.
[2]CPD plasma was separated form RBC (red blood cells) and then made to 1 Unit per ml plasma with sodium heparin. The plasma was then frozen (at −80° C.) and stored (at −60° C.) with cryoprecipitate prepared within 5 days. Approximately 9 mls volume was kept in each bag.
[3]% recovery compared to starting levels.

In the following Table 2, the recovering of Factor VIII is expressed per liter of starting plasma. It will be seen that the cold-insoluble globulin precipitate provides 666 units per liter of Factor VIII or a 62% recovery. This can be compared with the recovery reported by Fekete et al in column 5, Example 1 of the reissue patent previously mentioned. The 17% recovery in the final product obtained by Fekete represents only 170 units per liter of starting plasma.

TABLE 2

Recovery of Factor VIII Expressed per Liter of Starting Plasma*

| Fraction | Units/Liter | % Recovery |
|---|---|---|
| Plasma | 1069 | 100 |
| Cryoprecipitate Pool | 868 | 81 |
| Cold Insoluble Globulin Precipitate | 666 | 62 |

*Based on pools of 6 units of plasma

In the following Table 3, there is found an analysis of the total contents of the starting plasma fraction, cryoprecipitate pool fraction and cold-insoluble precipitate fraction.

TABLE 3

Purification of AHF from Cryoprecipitate by Cold-Incubation of the Cryoprecipitate at 0° C. for 2 hrs. in Presence of CSH Buffer[2]
Analysis of Total Contents

| Fraction[1] | Total Protein (mg) | Total Fibrinogen (mg) | Total Albumin (mg) | Antibody Titre | Volume (ml) |
|---|---|---|---|---|---|
| 1. Starting | 131,520 | 4404 | 65,906.4 | 1:32 | 1527 |

TABLE 3-continued

Purification of AHF from Cryoprecipitate by Cold-Incubation of the Cryoprecipitate at 0° C. for 2 hrs. in Presence of CSH Buffer[2]
Analysis of Total Contents

| Fraction[1] | Total Protein (mg) | Total Fibrinogen (mg) | Total Albumin (mg) | Antibody Titre | Volume (ml) |
|---|---|---|---|---|---|
| Plasma | (100%)[3] | (100%) | (100%) | Anti B | (100%) |
| 2. Cryoprecipitate Pool | 4770 (3.6%) | 424 (9.6%) | 1908 (2.9%) | 1:32 Anti B | 53 (3.5%) |
| 3. Cold-Insoluble Precipitate made from the cryoprecipitate | 1220 (0.9%) | 384 (8.7%) | 163 (.25%) | 1:16 Anti B | 11.3 (.74%) |

[1]Fraction 2 is obtained from Fraction 1, and Fraction 3 was obtained from Fraction 2.
[2]6 Bags of CPD plasma to which heparin was added to give 1 Unit Heparin/ml plasma. The 6 bags were pooled after cryoprecipitation.
[3]% recovery of component relative to the levels in the starting plasma. Protein was determined by Lowry assay with bovine serum albumin as standard. RID (Radial Immunodiffusion) plates for albumin or fibrinogen were used to determine the concentration of these components. Standard plasma containing known amounts of albumin and fibrinogen were provided by Behring Diagnostics.

Application of the cryoprecipitate-cold insoluble globulin procedure to citrate plasma obtained by plasmapheresis using the Haemonetics Model 50 machine with the plasma made to 1 unit of sodium heparin per ml of plasma also produces a Factor VIII concentrate of considerable potency. This technique results in the recovery of 81–83% of the initial plasma Factor VIII:C activity in the cryoprecipitate and an overall recovery in the final cold insoluble globulin precipitate of 56–62% of the initial plasma Factor VIII activity. The specific activity of the final product is 0.96–0.99 units/mg of protein with a 99–160 fold increase in purity compared to plasma. As indicated in Tables 4 and 5, the data indicate that, when using plasmapheresis plasma, it is possible to increase the recovery to produce a concentrate with a specific activity which qualifies the compound as high purity (greater than 1 unit/mg).

TABLE 4

Recovery of F.VIII:C/ml From Citrate and 1 Unit Heparin Per ml Pheresis Plasma by the Cold-Insoluble Cryoprecipitate Technique

| Sample | % F.VIII:C/ml | Volume | Total Units F.VIII:C | % Recovery Over Plasma | Unit/Liter Starting Plasma |
|---|---|---|---|---|---|
| Tubes: | | | | | |
| CPD Plasma | 60%/ml | — | — | — | — |
| Citrate Plasma | 60%/ml | — | — | — | — |
| Pheresis: | | | | | |
| Citrate Plasma and Heparin | 60%/ml | 2032 mls | 1219U | 100% | 600U/L |

TABLE 4-continued

Recovery of F.VIII:C/ml From Citrate and 1 Unit Heparin Per ml Pheresis Plasma by the Cold-Insoluble Cryoprecipitate Technique

| Sample | % F.VIII: C/ml | Volume | Total Units F.VIII:C | % Recovery Over Plasma | Unit/Liter Starting Plasma |
|---|---|---|---|---|---|
| (1 U/ml) Cryoprecipitate Pool | 1120%/ml | 85 mls | 1015U | 83% | 500U/L |
| Cold-Insoluble Cryoprecipitate (Washed) | 2520%/ml | 28.1 mls | 755U | 62% | 372U/L |

Four volunteers (3 O's, 1A) were plasmapheresed on a model 50 Haemonetics pheresis machine with 1 part 4 g% sodium citrate per 14 parts blood. They were also collected into CPD or citrate tubes as usual.

TABLE 5

Specific Activity of citrate and heparin pheresis plasma fractions

| Fraction | Total F.VIII:C | Total Protein (mg) | Specific Activity | Purity Over Plasma |
|---|---|---|---|---|
| Plasma (Citrate + 1 Unit Heparin/ml) | 1219U | 195,072 | 0.006U/mg | — |
| Cryoprecipitate Pool | 1015U | 5,032 | 0.201U/mg | 33.5x |
| Cold-Insoluble Cryoprecipitate | 755.3U | 786.8 | 0.96U/mg | 160x |

We claim:
1. A method of obtaining Factor VIII which comprises
   (a) adding heparin to freshly obtained blood plasma collected into a calcium chelating anticoagulant or collecting blood plasma by plasma pheresis using heparin and a calcium chelating anticoagulant;
   (b) freezing the plasma;
   (c) resolubilizing the plasma;
   (d) isolating a cryoprecipitate from the plasma;
   (e) resolubilizing the cryoprecipitate;
   (f) adding a citrate saline heparin buffer to the resolubilized cryoprecipitate;
   (g) incubating the buffered, resolubilized cryoprecipitate at a temperature of from about 0° to about 10° C. for a time in excess of about one hour, whereby Factor VIII present in the cryoprecipitate is insolubilized using heparin precipitable cold insoluble globulin and the resulting Factor VIII rich precipitate also includes cold insoluble globulin;
   (h) separating the Factor VIII rich precipitate; and
   (i) isolating Factor VIII therefrom.
2. A method as claimed in claim 1 wherein the calcium chelating anticoagulant is selected from citrate anticoagulants, ethylenediaminetetraacetic acid and oxalates.
3. A method as claimed in claim 1 wherein the calcium chelating anticoagulant is a citrate anticoagulant.
4. A method as claimed in claim 3 wherein the anticoagulant is acid-citrate-dextrose.
5. A method as claimed in claim 3 wherein the anticoagulant is citrate-phosphate-dextrose.
6. A method as claimed in claim 1 wherein the blood plasma is collected by plasmapheresis using heparin and sodium citrate.
7. A method of obtaining Factor VIII which comprises
   (a) adding heparin to freshly obtained blood plasma collected into a citrate-phosphate-dextrose anticoagulant or collecting blood plasma by plasmapheresis using heparin and sodium citrate anticoagulant;
   (b) freezing the plasma to about −80° C.;
   (c) resolubilizing the plasma at a temperature of from about 0° to about 10° C. for from about 30 to about 120 minutes;
   (d) centrifuging the resolubilized plasma to isolate a cryoprecipitate;
   (e) resolubilizing the cryoprecipitate at a temperature of about 37° C. for about 2–5 minutes;
   (f) adding from about 2 to about 10 ml of citrate saline heparin buffer per bag of the resolubilized cryoprecipitate;
   (g) incubating the buffered, resolubilized cryoprecipitate at about 0° C. for about two hours whereby Factor VIII present in the cryoprecipitate is insolubilized using heparin precipitate cold insoluble globulin and the resulting Factor VIII rich precipitate also includes cold insoluble globulin;
   (h) separating the Factor VIII rich precipitate; and
   (i) isolating the Factor VIII therefrom.
8. A method as claimed in claim 7 wherein the resolubilization of the plasma in step (c) is carried out at about 4° C. for about 75 minutes.
9. A method as claimed in claim 1, 7 or 8 wherein Factor VIII is isolated from the Factor VIII rich precipitate by washing the insoluble precipitate in the cold at a temperature of from about 0° to about 10° C. with citrate saline heparin buffer; draining the precipitate and resolubilizing it in the presence of further citrate saline heparin buffer.
10. A method as claimed in claim 1, 7 or 8 wherein the Factor VIII is isolated from the Factor VIII rich precipitate by washing the insoluble precipitate in the cold at about 0° C. with citrate saline heparin buffer; draining the precipitate and resolubilizing it at about 37° C. in the presence of further citrate saline heparin buffer.
11. A method as claimed in claim 1, 7 or 8 wherein the isolated Factor VIII is subjected to further purification procedures.
12. A method as claimed in claim 1, 7 or 8 wherein the isolated Factor VIII is subjected to further purification procedures selected from fractionation by precipitation by glycine, ethanol, ethanol-glycine, polyethylene glycol and glycine-polyethylene glycol precipitation.
13. A method as claimed in claim 1, 7 or 8 wherein Factor VIII is isolated from the Factor VIII rich precipitate by washing the insoluble precipitate in the cold at a temperature of from about 0° to about 10° C. with citrate saline heparin buffer; draining the precipitate and resolubilizing it in the presence of further citrate saline heparin buffer and the isolated Factor VIII is subjected to further purification procedures.

14. A method as claimed in claim 1, 7 or 8 wherein the Factor VIII is isolated from the Factor VIII rich precipitate by washing the insoluble precipitate in the cold at about 0° C. with citrate saline heparin buffer; draining the precipitate and resolubilizing it at about 37° C. in the presence of further citrate saline heparin buffer and the isolated Factor VIII is subjected to further purification procedures.

15. A method as claimed in claim 1, 7 or 8 wherein Factor VIII is isolated from the Factor VIII rich precipitate by washing the insoluble precipitate in the cold at a temperature of from about 0° to about 10° C. with citrate saline heparin buffer; draining the precipitate and resolubilizing it in the presence of further citrate saline heparin buffer and the isolated Factor VIII is subjected to further purification procedures selected from fractionation by precipitation by glycine, ethanol, ethanol-glycine, polyethylene glycol and glycine-polyethylene glycol precipitation.

16. A method as claimed in claim 1, 7 or 8 wherein the Factor VIII is isolated from the Factor VIII rich precipitate by washing the insoluble precipitate in the cold at about 0° C. with citrate saline heparin buffer; draining the precipitate and resolubilizing it at about 37° C. in the presence of further citrate saline heparin buffer and the isolated Factor VIII is subjected to further purification procedures selected from fractionation by precipitation by glycine, ethanol, ethanol-glycine, polyethylene glycol and glycine-polyethylene glycol precipitation.

* * * * *